United States Patent [19]

Rich et al.

[11] Patent Number: 4,952,708

[45] Date of Patent: Aug. 28, 1990

[54] METHOD FOR PREPARING BIARYL COMPOUNDS

[75] Inventors: Jonathan D. Rich, Rexford; Terry E. Krafft, Schenectady; Philip J. McDermott, Troy, all of N.Y.; Tony C. Chang, Ohta, Japan

[73] Assignee: General Electric Company, Schenectady, N.Y.

[21] Appl. No.: 331,774

[22] Filed: Apr. 3, 1989

Related U.S. Application Data

[63] Continuation-in-part of Ser. No. 187,783, Apr. 29, 1988, abandoned.

[51] Int. Cl.$^5$ .................. C07C 69/78; C07D 307/89
[52] U.S. Cl. .................. 549/241; 548/455; 548/518; 549/472; 549/59; 558/360; 560/96; 562/853; 562/840; 564/153; 568/312; 568/931; 570/142; 570/161
[58] Field of Search .............. 548/455, 518; 549/241, 549/472, 59; 558/360; 560/96; 564/153; 568/312, 931; 570/142, 161; 260/544 L, 544 P, 544 Y; 562/840, 853

[56] References Cited

U.S. PATENT DOCUMENTS

| | | | |
|---|---|---|---|
| 2,809,210 | 10/1957 | Short et al. | 562/482 |
| 4,292,435 | 9/1981 | Itatani et al. | 560/96 |
| 4,338,456 | 7/1982 | Itatani et al. | 560/96 |
| 4,581,469 | 4/1986 | Itatani et al. | 560/96 |
| 4,604,477 | 8/1986 | Rich | 556/436 |
| 4,709,054 | 11/1987 | Rich | 549/214 |

FOREIGN PATENT DOCUMENTS 61-167642  7/1986  Japan.

OTHER PUBLICATIONS

*Journal of Organometallic Chemistry*, T. Mitchell, "Transition–Metal Catalysts in Organotin Chemistry", (1986), pp. 1, 7–8.
*Chemical Abstracts*, "Biphenyltetracarboxylic Dianhydrides", Itatani, vol. 80, 1974.
*J. Org. Chem.*, Iataaki et al., "Palladium–Catalyzed Syntheses of Aromatic Coupling Compounds", vol. 38, No. 1 (1973), pp. 76–79.
*Advanced Organic Chemistry*, J. March, 2nd Ed., McGraw Hill (1977), pp. 490, 606–607, 653–654, 656–657, 664,665.
*Journal of Organometallic Chemistry*, 282 (1985), N. Bumagin et al., "Reactions of Organometallic Compounds Catalyzed by Transition–Metal Complexes", pp. 421–425.
*J. Am. Chem. Soc.*, 1987, 109, Echavarren et al., "Palladium–Catalyzed Coupling of Aryl Triflates With Organostannanes", pp. 5478–5486.

*Primary Examiner*—Richard L. Raymond
*Attorney, Agent, or Firm*—William H. Pittman; James C. Davis, Jr.

[57] ABSTRACT

An improved method for making biaryl compounds is disclosed, in which an aromatic acid halide having at least one strong electron-withdrawing group attached to or within the aromatic ring is reacted with at least one polysilane in the presence of an effective amount of a transition metal catalyst.

27 Claims, No Drawings

METHOD FOR PREPARING BIARYL COMPOUNDS

This application is a continuation-in-part of copending application Ser. No. 187,783, filed Apr. 29, 1988, now abandoned.

This invention relates generally to the reductive coupling of acid halides, and more particularly to an improved method for preparing biaryl compounds, such as biphenyl dianhydride.

Functionalized biaryl compounds are of considerable interest as intermediates in polymer synthesis. For example, they may be used in the preparation of many thermoplastics, such as polyesters, polycarbonates, polyethers, and polyimides.

Some methods for forming biaryl compounds are known in the art. For example, the Scholl reaction couples two aromatic molecules by treatment with a Lewis acid and a proton acid. The Ullman reaction involves the coupling of aryl halides by treatment with copper or nickel. The Gomberg-Bachmann reaction couples the aryl portion of a diazonium salt with another aromatic ring to yield biaryl compounds. Other methods include the coupling of organometallic species such as Grignard reagents, arylthallium, arylcopper, or arylmercury compounds. Moreover, N. A. Bumagin et al. describe the formation of biaryl derivatives as by-products in the palladium-catalyzed reaction of aromatic acid chlorides with hexaethylditin. *J. Organometallic Chem.*, Vol. 282, 1985, pp. 421-425. Also, Echavarren and Stille report the coupling of aryltriflates by treatment with ditin compounds and a palladium catalyst. *J. Am. Chem. Soc.*, 1987, 109, pp. 5478-5486.

As yet another example, H. Iataaki et al. teach the oxidative coupling of aromatic compounds under oxygen pressure in the presence of palladium acetate to form various biaryl compounds. *J. Org. Chem.*, Vol. 38, No. 1, 1973, pp. 76-79. Furthermore, in U.S. Pat. No. 4,292,435 of H. Itatani et al., biphenyltetracarboxylic esters are prepared by oxidatively coupling an orthophthalic diester in a molecular oxygen-containing atmosphere in the presence of certain palladium salt-based catalysts. Another process is disclosed by R. Short et al. in U.S. Pat. No. 2,809,210, and calls for reacting halides of mononuclear carboxylic aromatic compounds with methanol in the presence of a suitable catalyst, wherein the methanol is added gradually to a mixture of the other reactants.

While all of the above-described reactions do result in the production of some biaryl, they are deficient for at least one of several reasons. For example, many of the reactions suffer from high cost or low yield of biaryl Furthermore, a drawback involved in the synthesis described by Iataaki et al. is the required use of high oxygen pressures, which could pose safety hazards. Moreover, that type of reaction and some of the others mentioned above are sometimes not highly selective for a particular isomeric product that might be much more commercially valuable than the other isomers.

An additional disadvantage attendant with some of these reactions is that their use results in salts such as metal halides as by-products. Such by-products are troublesome from both a processing and an environmental standpoint, and additional procedures are required for their neutralization and removal.

In U.S. Pat. No. 4,709,054, there is disclosed the reaction of various polysilanes, especially those containing halogen substituents on silicon, with aromatic acyl halides to form arylsilanes. This reaction takes place in the presence of a transition metal catalyst, preferably a palladium compound, under various temperatures and other conditions.

It has now been discovered that under certain conditions, said reaction also produces biaryls, frequently in appreciable yields. Thus, the conditions of the catalyzed silane-acyl halide reaction can in certain instances be varied to yield said biaryls as easily recoverable products. High-pressure conditions are not necessary. The method is particularly adaptable to the preparation of 3,4,3',4'-biphenyltetracarboxylic acid dianhydride and 4,4'-biphenyldicarboxylic acid chloride.

Accordingly, the invention is a method for making biaryl compounds which comprises (A) reacting an aromatic acid halide having at least one strong electron-withdrawing group attached to or within the aromatic ring with at least one polysilane as described below, in the presence of an effective amount of at least one transition metal catalyst; and (B) recovering the biaryl compound from the mixture resulting from step A.

Among the desirable products which may be prepared from this process are 3,4,3',4'-biphenyltetracarboxylic acid dianhydride (commonly referred to as biphenyl dianhydride), 3,3'-dinitrobiphenyl and 4,4'-biphenyldicarboxylic acid chloride.

The term "biaryl compounds" as used herein is meant to describe compounds which contain a biaryl group, e.g., the biphenylyl radical

  (I)

or the radical

  (II)

where Y is either —O—, —S—, or

as described below. Biaryl compounds are well-known in the art Some of these are described, for example, by R. Short in U.S. Pat. No. 2,809,210, incorporated herein by reference. Itatani et al. describe biaryl compounds in U.S. Pat. Nos. 4,292,435, 4,338,456 and 4,581,469, each of which is also incorporated herein by reference.

The aromatic acid halides used in the method of this invention may be represented by the formulas

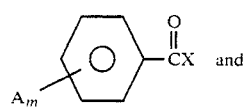  (III)

and

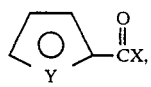

(IV)

wherein X is halogen; A is a strong electron-withdrawing group; Y is a strong electron-withdrawing group selected from the group consisting of oxygen, sulfur and

and m is at least 1.

The electronic effects of electron-withdrawing groups are known in the art and described, for example, by Morrison and Boyd in *Organic Chemistry*, Third Edition, Allyn and Bacon, Inc., the relevant contents of which are incorporated herein by reference. The term "strong electron-withdrawing group" as used herein includes the following groups, with examples of suitable compounds containing such groups being provided.

TABLE I

| Group | Unit Structure | Examples For This Invention |
|---|---|---|
| Nitro | $-NO_2$ | 3-nitrobenzyl chloride |
| Anhydride | (structure) | Trimellitic anhydride acid chloride |
| Imide | (structure) | N-n-Butyltrimellitimide acid chloride |
| Amide | $R_2N-\overset{O}{\underset{\|}{C}}-$ | (structure) |
| Halogen | F, Cl, I, Br | Pentafluorobenzoyl chloride |
| Cyano | $N\equiv C-$ | 3,5-Dicyanobenzoyl chloride |
| Acyl | (structure) | (structure) |

TABLE I-continued

| Group | Unit Structure | Examples For This Invention |
|---|---|---|
| Carbonyl halide | $-\overset{O}{\underset{\|}{C}}X$ | Terephthaloyl chloride |
| Ester | $-\overset{O}{\underset{\|}{C}}-OR$ | (structure) |
| Oxygen | $-O-$ | (structure) |
| Sulfur | $-S-$ | (structure) |
| $\underset{/}{\overset{\backslash}{}}NH$ | $\underset{/}{\overset{\backslash}{}}NH$ | (structure) |

In these formulas, each R is independently halogen or a monovalent $C_{1-12}$ aliphatic, alicyclic, or aromatic hydrocarbon group, with $C_{1-3}$ groups being preferred. The value of m may be from 1 to 5 and is usually 1.

Those of ordinary skill in the art understand that the selection of Y for formula IV determines which particular compound of formula II is to be prepared. Illustrative compounds of formula II are bifuran compounds, bipyrrole compounds, and bithiophene compounds.

The choice of a particular aromatic acid halide depends in part on the desired product. For example, trimellitic anhydride acid chloride (i.e., 1,2,4-benzenetricarboxylic anhydride chloride) would be a suitable reactant in the preparation of 3,4,3',4'-biphenyltetracarboxylic acid dianhydride, as further described below. As a further illustration, 3-nitrobenzoyl chloride and terephthaloyl chloride would be suitable reactants for the preparation of 3,3'-dinitrobiphenyl and 4,4'-biphenyldicarboxylic acid chloride, respectively, while 2-furanoyl chloride would be suitable for the production of 2,2'-bifuran.

Polysilanes suitable in the method of the present invention have the formula $$R'-\left[\begin{matrix} R' \\ | \\ Si \\ | \\ R' \end{matrix}\right]_n \begin{matrix} R' \\ | \\ Si-R', \\ | \\ R' \end{matrix} \qquad (V)$$

wherein each R' is individually selected from the group consisting of halogen, hydrogen, alkyl groups containing from about 1 to 10 carbon atoms, aromatic groups containing from about 6 to 20 carbon atoms, alkoxy groups containing from about 1 to 10 carbon atoms, and aryloxy groups containing from about 6 to 20 carbon atoms, with n being an integer in the range of about 1 to 50. Polysilanes of this type are known in the art and described, for example, in the aforementioned U.S. Pat. No. 4,709,054, incorporated herein by reference. Some of these compounds are also described by C. Eaborn in *Organosilicon Compounds*, Butterworths Publications Limited, 1960.

In preferred embodiments the value of n is about 1 to 10, and most preferably, is 1. Furthermore, at least two of the R groups in formula V are preferably methyl, ethyl, or phenyl.

A specific preferred group of polysilanes includes hexamethyldisilane; hexaethyldisilane; hexaphenyldisilane; 1,2-diphenyltetramethyldisilane; 1,2-dichlorotetramethyldisilane; 1,1,2,2-tetrachlorodimethyldisilane; 1,1,2-trichlorotrimethyldisilane; and 1-monochloropentamethyldisilane. It should also be understood that mixtures of any of the silanes of formula V may be used.

A particularly suitable source of a mixture of polysilanes is that obtained in a process for making dimethyldichlorosilane, which is an important precursor for many silicone polymers. This process comprises the reaction of an alkyl chloride such as methyl chloride with silicon at temperatures above about 250° C. in the presence of a metal catalyst (such as copper) to form a mixture comprising dimethyldichlorosilane and a high-boiling (greater than about 100° C.) by-product stream containing a mixture of halogenated polysilanes, in which each n value of formula V is 1, and at least two of the R groups are methyl or ethyl. Such a reaction is generally described in more detail by C. Eaborn in the above-mentioned text, and in the following U.S. Patents, each of which is incorporated herein by reference: E. Rochow, U.S. Pat. Nos. 2,380,945; W. Patnode, 2,380,997; and Rochow et al., 2,380,996.

Thus, the present invention includes an improved method for making dimethyldichlorosilanes, in which the halogenated polysilane by-product is reacted with an aromatic acid halide of formula III or IV to form a product mixture comprising a biaryl compound and a low boiling (less than about 100° C.) silane compound. Furthermore, when trimellitic anhydride acid chloride is reacted with 1,2-dichlorotetramethyldisilane in the last-mentioned reaction to make 3,4,3',4'-biphenyltetracarboxylic acid dianhydride, dimethyldichlorosilane is a by-product which can itself be used as described above.

The polysilanes function as reducing agents in this process. Thus, the aromatic acid halides described above are reductively coupled while the addition of silicon to the aromatic ring is minimized, thereby ensuring the recovery of a maximum of biaryl product.

The molar ratio of aromatic acid halide to polysilane is usually in the range of about 2:1 to about 0.5:1. In preferred embodiments, a molar excess of aromatic acid halide is used, e.g., a molar ratio of at least about 1.1:1, and most preferably, at least about 1.5:1.

As mentioned above, a transition metal catalyst is employed to catalyze the reaction of the present invention. Transition metal catalysts suitable for use herein are described in the aforementioned U.S. Pat. No. 4,709,054. Various palladium-containing catalysts are preferred, including bis(benzonitrile)palladium dichloride, bis(acetonitrile)palladium dichloride, allylpalladium chloride dimer, bis(triphenylphosphine)palladium dibromide, palladium dichloride, palladium on carbon, palladium on silica, and mixtures thereof. The preferred transition metal catalyst is bis(benzonitrile)palladium dichloride. An effective amount of the catalyst is usually about 0.001% by weight to about 1.0% by weight, based on the weight of the aromatic acid halide.

An amine or phosphine cocatalyst is frequently used to enhance the action of the main catalyst. Examples of cocatalysts are given in U.S. Pat. No. 4,709,054, and include trimethylamine, tributylamine, pyridine, triphenylphosphine, and tributylphosphine, with triphenylphosphine being most preferred. An effective amount of the cocatalyst is usually from about 0.001% to about 1.0% by weight, based on the weight of the aromatic acid halide.

A very suitable catalyst/cocatalyst system contains bis(benzonitrile)palladium dichloride and triphenylphosphine in a weight ratio of about 10:1 to about 1:2, respectively, and most preferably, about 1:1.4.

Reaction of the aromatic acid halide with the polysilane may take place in the absence of solvent by simply heating the reagents above their melting points. However, the reaction is preferably carried out in the presence of solvent while stirring the reactants under an inert atmosphere such as nitrogen. In this embodiment, the reaction must be carried out in an aprotic nonpolar solvent medium. Examples of these solvents are alkylated benzenes with boiling points higher than about 100° C., such as mesitylene, durene, xylene, and toluene. Alkoxy-substituted phenyl compounds can also be used, such as anisole. Petroleum ethers with boiling points above about 100° C., such as nonane, n-decane, and n-dodecane, are also effective. Of course, mixtures of the above solvents are also possible. The following represents a preferred group of reaction solvents: toluene, mesitylene, nonane, xylene, anisole, durene, and mixtures thereof. The amount of solvent employed depends on processing conditions, such as the desired viscosity, and can be determined by those of ordinary skill in the art without undue experimentation.

In general, higher reaction temperatures result in greater yield of the biaryl product, and minimize the yield of by-products, such as silylated aromatic compounds. Thus, reaction temperatures of at least about 130° C. are employed, while temperatures of at least about 145° C. are preferred. Frequently, reaction temperatures in the range of about 160° C.–180° C. are employed.

Other reaction techniques suitable for the present method are discussed in U.S. Pat. No. 4,709,054. One technique of some interest involves heating the reactants above their melting temperature and then flowing the liquid reactant mix over a catalyst (for example, palladium) which is bound to an inert support material such as silica or carbon. In preferred embodiments, the reactants are dissolved in one or more of the solvents discussed above before being passed over the catalyst.

The recovery technique should be one that can collect substantially all of the biaryl product formed, while leaving behind any silylated aromatic by-products which mixture is first cooled to room temperature after the reaction is deemed substantially complete. The extent of reaction can be determined by several methods, e.g., monitoring by-product gas evolution, or by the use of gas chromatography to measure how much of the reagents remain. Filtration is the preferred product isolation method, and is described in some detail in volume 10 of the *Kirk-Othmer Encyclopedia of Chemical Technology*. 3rd Edition, pages 284–337, and in other references mentioned therein. Cannister and centrifuge filtration are both particularly good techniques for recovering biaryl product produced by this method.

After filtration, the biaryl product can be washed with a suitable solvent, such as methylene chloride, chloroform, toluene, or acetone.

An exemplary reaction according to the present invention is as follows:

STEP 1

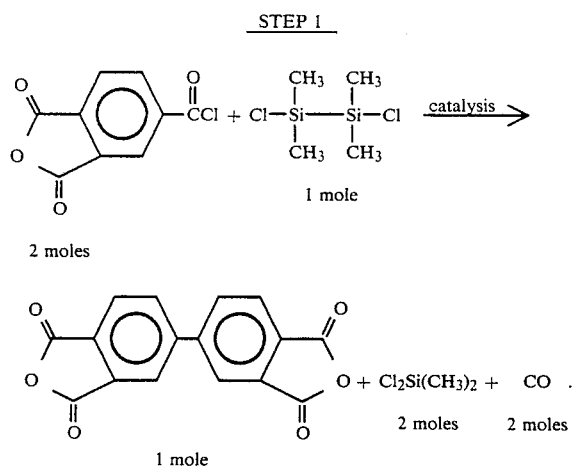

STEP 2

Cool reaction mixture, remove volatile components under vacuum, isolate biaryl product by filtration, and then wash with methylene chloride.

As described in the examples, this particular reaction results in an 85% yield of 3,4,3',4'-biphenyltetracarboxylic acid dianhydride (based on theoretical moles of product) when reaction temperatures of about 160° C. are used. A yield of 70% or more is considered "high" for the present invention.

Those of ordinary skill in the art appreciate that the other aromatic acid chlorides mentioned above may be reacted in analogous fashion to form a particular desired biaryl compound or isomer thereof. For example, the product 3,3'-dinitrobiphenyl may be prepared by the use of 3-nitrobenzoyl chloride as the aromatic acid halide. Furthermore, 2,2'-bifuran may be prepared by the use of 2-furanoyl chloride as the aromatic acid halide.

The following examples describe some embodiments of the present invention. However, the invention is not intended to be limited in any way by these examples. Product yield is based on theoretical yield according to molar proportions used. Percentages are by weight, unless otherwise indicated.

EXAMPLE 1

A 50 mL round bottom flask was charged with trimellitic anhydride acid chloride (10.53 g., 0.05 mole), bisbenzonitrile palladium dichloride (Pd(PhCN)$_2$Cl$_2$) (19.2 mg., $5.0 \times 10^{-5}$ mole), triphenylphosphine (26.2 mg., $1.0 \times 10^{-4}$ mole) and dry mesitylene (10 mL). The mixture was heated under a nitrogen atmosphere to approximately 160° C. Visible gas evolution began immediately upon addition of 1,2-dichlorotetramethyldisilane (4.68 g., 0.025 mole). After 2 hours, an additional alliquot of disilane (4.68 g.) was added. After heating for a total of 16 hours, the mixture was cooled, and the volatile components and solvent were removed under vacuum. The desired 3,4,3',4'-biphenyltetracarboxylic acid dianhydride was isolated by filtration and washed with methylene chloride. The isolated material weighed 5.30 g., i.e., a 72% yield. The identity of the product was confirmed by the use of 1H NMR (nuclear magnetic resonance). A recrystallized sample was further characterized by mass spectroscopy, infrared analysis, and melting point. The melting point was 296°–298° C. The literature melting point is 298.5° C.

EXAMPLE 2

A mixture of trimellitic anhydride acid chloride (10.53 g., 0.05 mole), Pd(PhCN)$_2$Cl$_2$ (19.2 mg., $5.0 \times 10^{-5}$ mole), bis(diphenylphosphino)methane (19.2 mg., $5.0 \times 10^{-5}$ mole) and dry mesitylene (10 mL) was placed in a 50 mL round bottom flask fitted with a Vigreux column, Claisen tube and distilling head. The mixture was heated to 165°–C. under a nitrogen atmosphere, and 1,2-dichlorotetramethyldisilane (9.36 g., 0.05 mole) was then added with stirring. The mixture was heated for 18 hours and then cooled, and the volatile components were removed under vacuum. The solids were collected by filtration and washed with methylene chloride and carbon tetrachloride to yield 6.24 g. (85%) of the desired 3,4,3',4'-biphenyltetracarboxylic acid dianhydride.

EXAMPLE 3

A mixture of trimellitic anhydride acid chloride (10.53 g., 0.05 mole), Pd(PhCN)$_2$Cl$_2$ (19.2 mg., $5.0 \times 10^{-5}$ mole), triphenylphosphine (26.2 mg., $1.0 \times 10^{-4}$ mole) and dry mesitylene (8 mL) was placed in a 50 mL round bottom flask fitted with a Vigreux column, Claisen tube and distilling head. The mixture was heated under a nitrogen atmosphere in an oil bath at 185° C. Hexamethyldisilane (7.32 g., 0.05 mole) was added over a 4.5 hour period. After a total of 6 hours, the mixture was cooled. The product was then isolated by filtration and washed with methylene chloride and acetone. A total of 5.59 g. of the desired 3,4,3',4'-biphenyltetracarboxylic acid dianhydride was obtained, for a yield of 76%.

EXAMPLE 4

A 50 mL round bottom flask was charged with trimellitic anhydride acid chloride (10.53 g.), Pd(PhCN)$_2$Cl$_2$ (19.2 mg.), triphenylphosphine (23.6 mg.) and dry mesitylene (10 mL). The mixture was heated to 150° C. under a nitrogen atmosphere. A crude mixture of disilanes (11.03 g., 0.05 mole), obtained as a by-product in the preparation of dimethyldichlorosilane and consisting of 72% tetrachlorodimethyldisilane, 19% trichlorotrimethyldisilane, and 9% dichlorotetramethyldisilane, was added over a 2-hour period. After a total of 20 hours, the desired 3,4,3',4'-biphenyltetracarboxylic acid dianhydride was isolated as in Example 1. The product weighed 2.28 g., for a yield of 31%.

EXAMPLE 5

A mixture of 3-nitrobenzoyl chloride (9.28 g., 0.05 mole), Pd(PhCN)$_2$Cl$_2$ (19.2 mg.), triphenylphosphine (26.2 mg.) and dry mesitylene (10 mL) was heated to 160° C. 1,2-Dichlorotetramethyldisilane (9.36 g., 0.05 mole) was added to the mixture over a 4 hour period. After a total of 6 hours, the reaction mixture was cooled, and the volatile components were removed under vacuum. The product was removed by filtration and then washed with carbon tetrachloride and hexane. Upon recrystallization from hot acetone, the desired 3,3'-dinitrobiphenyl was obtained as a white crystalline solid product weighing 1.64 g., for a yield of about 27%.

The compound was characterized by $^1$H NMR, infrared spectroscopy, mass spectroscopy, and melting point. The melting point was about 197°–200° C. The literature melting point is 200° C.

EXAMPLE 6

A reaction mixture containing 2-furanoyl chloride (5.0 g., $3.8 \times 10^{-2}$ mole) and 1,2-dichlorotetramethyldisilane
(7.6 g., $3.8 \times 10^{-2}$ mole) was heated to 145° C. under an atmosphere of dry nitrogen. A catalyst mixture containing Pd(PhCN)$_2$Cl$_2$ (26 mg.) and triphenylphosphine (33 mg.) was added to the reaction mixture, which was then heated at 145° C. for 15 hours. Fractional distillation (boiling point 55° C./60 torr) resulted in the recovery of 2,2′-bifuran weighing 2.05 g., representing an 80% yield. The product was characterized by $^1$H NMR, as well as infrared and mass spectroscopy.

EXAMPLE 7

A mixture of 10.46 grams (50 mmol.) of terephthaloyl chloride, 19.2 mg. of Pd(PhCN)$_2$Cl$_2$, 26.2 mg. of triphenylphosphine and 10 mL of dry mesitylene was heated to 165° C. and 9.36 grams (50 mmol.) of 1,2-dichlorotetramethyldisilane was added over 2 hours, with stirring. Stirring and heating were continued for 24 hours, after which the mixture was cooled and diluted with 15 ml. of pentane. It was then cooled at −10° C. for several hours, whereupon the desired 4,4′-biphenyldicarboxylic acid chloride separated and was removed by filtration and washed with pentane. It was identified by proton nuclear magnetic resonance, infrared and mass spectroscopy. The yield was 1.49 grams, or 21.4% of theoretical.

What is claimed is:

1. A method for making biaryl compounds which comprises:

(A) reacting, in an inert atmosphere, an aromatic acid halide having at least one strong electron-withdrawing group attached to or within the aromatic ring with at least one polysilane of the formula $$R'-\left(\begin{array}{c} R' \\ | \\ Si \\ | \\ R' \end{array}\right)_n \begin{array}{c} R' \\ | \\ Si-R' \\ | \\ R' \end{array} \quad (V)$$

at a temperature of at least about 145° C., in the presence of an aprotic nonpolar solvent and a catalytic amount of at least one transition metal complex, and (B) recovering a biaryl compound from the mixture resulting from step A;

wherein each R′ is independently selected from the group consisting of halogen, hydrogen, alkyl groups containing from about 1 to 10 carbon atoms, aromatic groups containing from about 6 to 20 carbon atoms, alkoxy groups containing from about 1 to 10 carbon atoms, and aryloxy groups containing from about 6 to 20 carbon atoms, and n is an integer in the range of about 1 to 50.

2. The method of claim 1 wherein recovery is effected by cooling the mixture resulting from step A after reaction is substantially complete, and the isolating said biaryl compound by filtration.

3. The method of claim 2 wherein the recovery step further includes washing of the filtered product with a solvent.

4. The method of claim 3 wherein the solvent used for washing is selected from the group consisting of methylene chloride, chloroform, toluene and acetone.

5. The method of claim 1 wherein the molar ratio of aromatic acid halide to total polysilane is at least about 1.1:1.

6. The method of claim 1 wherein the polysilane is a by-product stream from the reaction of an alkyl chloride with silicon.

7. The method of claim 1 wherein the strong electron-withdrawing group is selected from the group consisting of nitro, anhydride, halogen, imide, ami acyl, carbonyl halide, ester, oxygen, sulfur, and $$\diagdown \!\!\!\! \diagup \text{NH}.$$

8. The method of claim 1 wherein the strong electron-withdrawing group is selected from the group consisting of nitro, carbonyl halide and anhydride.

9. The method of claim 1 wherein n is 1, and at least two of the R′ groups are methyl, ethyl or phenyl.

10. The method of claim 9 wherein the polysilane is selected from the group consisting of hexamethyldisilane, 1,2-dichlorotetramethyldisilane, 1,1,2,2-tetrachlorodimethyldisilane, 1,1,2-trichlorotrimethyldisilane, 1-monochloropentamethyldisilane, and mixtures thereof.

11. The method of claim 9 wherein the polysilane is selected from the group consisting of hexamethyldisilane, hexaethyldisilane, hexaphenyldisilane, and 1,2-diphenyltetramethyldisilane.

12. The method of claim 11 wherein the transition metal catalyst is selected from the group consisting of bis(benzonitrile)palladium dichloride, bis(acetonitrile)palladium dichloride, allylpalladium chloride dimer, bis(triphenylphoshpine)palladium dibromide, palladium dichloride, palladium on carbon, palladium on silica, and mixtures thereof.

13. The method of claim 12 wherein the catalyst is present at about 0.001% by weight to about 1.0% by weight, based on the weight of the aromatic acid halide.

14. The method of claim 13 wherein the reaction mixture also contains an amine or phosphine cocatalyst.

15. The method of claim 14 wherein the cocatalyst is present at about 0.001% to about 1.0% by weight, based on he weight of the aromatic acid halide.

16. The method of claim 1 wherein a molar excess of acid halide is used and the reaction temperature is at least about 160° C.

17. The method of claim 1 wherein the nonpolar aprotic solvent is selected from the group consisting of toluene, mesitylene, nonane, xylene, anisole, durene, and mixtures thereof.

18. The method of claim 17 wherein the reaction temperature is at least about 160° C.

19. The method of claim 1 wherein the aromatic acid halide is trimellitic anhydride acid chloride.

20. The method of claim 1 wherein the aromatic acid halide is 3-nitrobenzoyl chloride.

21. The method of claim 1 wherein the aromatic acid halide is terephthalcyl chloride.

22. A method for forming biaryl compounds which comprises the reductive coupling in an inert atmosphere of an aromatic acid halide having an effective number of electron-withdrawing groups attached to or within the aromatic ring, by the use of a polysilane reducing agent of the formula

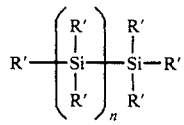
(V)

at a temperature of at least about 145° C., in the presence of an aprotic nonpolar solvent and an effective amount of at least one transition metal catalyst, wherein silicon addition to said aromatic ring is minimized;

each R' being independently selected from the group consisting of halogen, hydrogen, alkyl groups containing from about 1 to 10 carbon atoms, aromatic groups containing from about 6 to 20 carbon atoms, alkoxy groups containing from about 1 to 10 carbon atoms, and aryloxy groups containing from about 6 to 20 carbon atoms, and n is an integer in the range of about 1 to 50.

23. The method of claim 22 wherein the aromatic acid halide is trimellitic anhydride acid chloride.

24. A method for making 2,2'-bifuran which comprises:
(A) reacting 2-furanoyl chloride with at least one polysilane of the formula

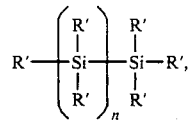
(V)

in the presence of a catalytic amount of at least one transition metal complex, and
(B) recovering 2,2'-bifuran from the mixture resulting from step A;

wherein each R' is independently selected from the group consisting of halogen, hydrogen, alkyl groups containing from about 1 to 10 carbon atoms, aromatic groups containing from about 6 to 20 carbon atoms, alkoxy groups containing from about 1 to 10 carbon atoms, and aryloxy groups containing from about 6 to 20 carbon atoms, and n is an integer in the range of about 1 to 50.

25. The method of claim 24 wherein the polysilane is selected from the group consisting of hexamethyldisilane, 1,2-dichlorotetramethyldisilane, 1,1,2,2-tetrachlorodimethyldisilane, 1,1,2-trichlorotrimethyldisilane, 1-monochloropentamethyldisilane, and mixtures thereof.

26. The method of claim 25 wherein the transition metal catalyst is selected from the group consisting of bis(benzonitrile)palladium dichloride, bis(acetonitrile)palladium dichloride, allylpalladium chloride dimer, bis(triphenylphosphine)palladium dibromide, palladium dichloride, palladium on carbon, palladium on silica, and mixtures thereof.

27. The method of claim 26 wherein the reaction mixture also contains an amine or phosphine cocatalyst.

* * * * *